(12) United States Patent
Zhao et al.

(10) Patent No.: US 10,345,242 B2
(45) Date of Patent: Jul. 9, 2019

(54) REVERSE INTENSITY CORRECTION FOR RAMAN SPECTRAL LIBRARY SEARCH

(71) Applicants: Jun Zhao, The Woodlands, TX (US); Xin Jack Zhou, Hockessin, DE (US)

(72) Inventors: Jun Zhao, The Woodlands, TX (US); Xin Jack Zhou, Hockessin, DE (US)

(73) Assignee: B&W TEK LLC, Washington, DC (US)

( * ) Notice: Subject to any disclaimer, the term of this patent is extended or adjusted under 35 U.S.C. 154(b) by 0 days.

(21) Appl. No.: 15/721,993

(22) Filed: Oct. 2, 2017

(65) Prior Publication Data

US 2018/0128747 A1 May 10, 2018

Related U.S. Application Data

(60) Provisional application No. 62/418,828, filed on Nov. 8, 2016.

(51) Int. Cl.
| | |
|---|---|
| *G01J 3/44* | (2006.01) |
| *G01N 21/65* | (2006.01) |
| *G01N 21/27* | (2006.01) |
| *G01N 21/3577* | (2014.01) |
| *G01N 21/359* | (2014.01) |
| *G01N 21/47* | (2006.01) |

(52) U.S. Cl.
CPC ........... *G01N 21/65* (2013.01); *G01N 21/274* (2013.01); *G01N 21/278* (2013.01); *G01N 21/359* (2013.01); *G01N 21/3577* (2013.01); *G01N 21/4785* (2013.01); *G01N 2021/656* (2013.01)

(58) Field of Classification Search
CPC ........ G01J 3/02; G01J 3/44; G01N 2021/656; G01N 21/65; G01N 21/658
USPC .......................................................... 356/301
See application file for complete search history.

(56) References Cited

U.S. PATENT DOCUMENTS

| | | | | |
|---|---|---|---|---|
| 5,455,673 A | * | 10/1995 | Alsmeyer ................. | G01J 3/44 356/301 |
| 5,710,713 A | * | 1/1998 | Wright ................. | G01N 21/274 250/282 |
| 5,850,623 A | * | 12/1998 | Carman, Jr. ............. | G01J 3/28 250/252.1 |
| 6,281,971 B1 | * | 8/2001 | Allen ........................ | G01J 3/02 356/301 |
| 7,664,605 B2 | | 2/2010 | Chaiken et al. | |
| 8,781,757 B2 | | 7/2014 | Farquharson et al. | |
| 9,194,803 B2 | | 11/2015 | Maquelin et al. | |
| 2008/0034833 A1 | * | 2/2008 | Maier ....................... | G01J 3/02 73/1.01 |

* cited by examiner

*Primary Examiner* — Md M Rahman
(74) *Attorney, Agent, or Firm* — Rimon PC

(57) ABSTRACT

This invention discloses a Reverse Intensity Correction method for spectral library search to correct for instrument response without the side effect of magnifying the noise in the low responsivity region of test spectra. Instead of applying relative intensity correction to the sample test spectra to match the standardized library spectra, a reverse intensity correction is applied to the standardized library spectra to match the uncorrected sample spectrum. This simple procedural change improves library search performance, especially for dispersive CCD Raman analyzers using NIR excitations, where the instrument response often varies greatly across the spectral range, and SNR in the low responsivity regions is typically poor.

18 Claims, 6 Drawing Sheets

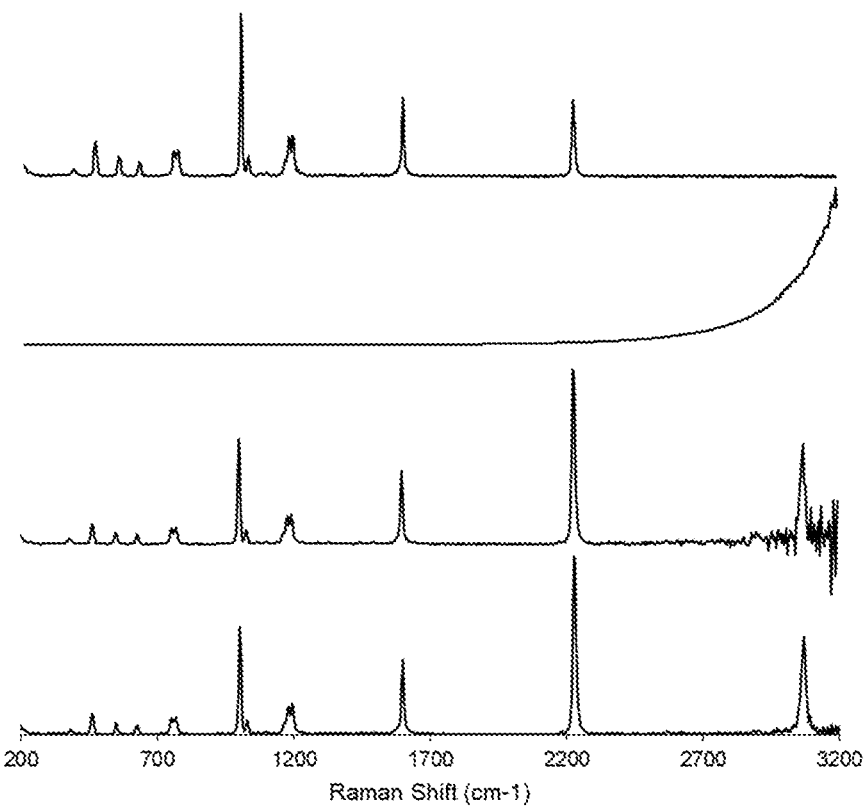
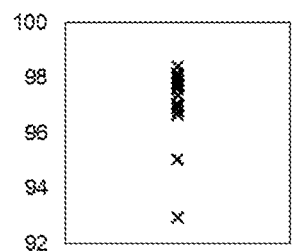# 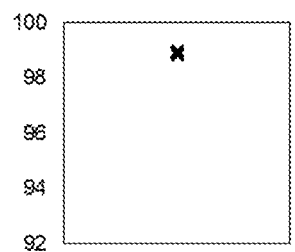
FIG. 1e  FIG. 1f

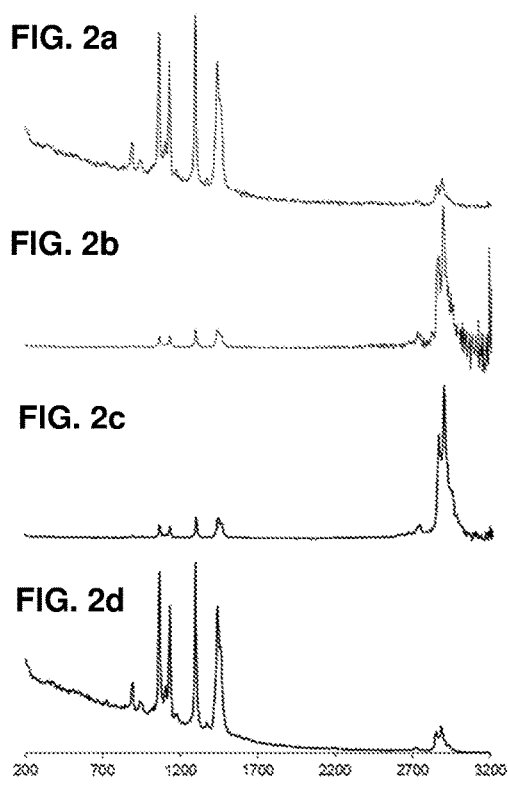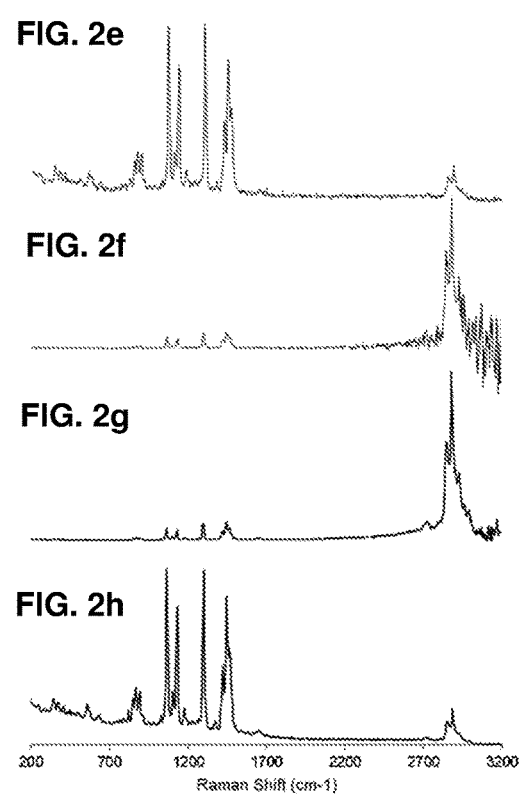

+ Stearic Acid Reference    x Mg Stearate Reference

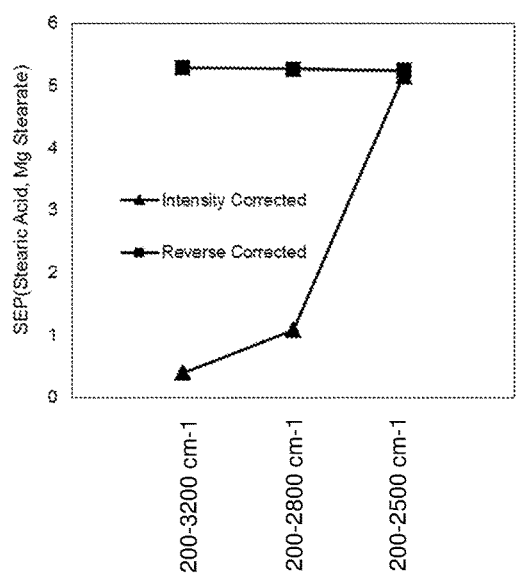 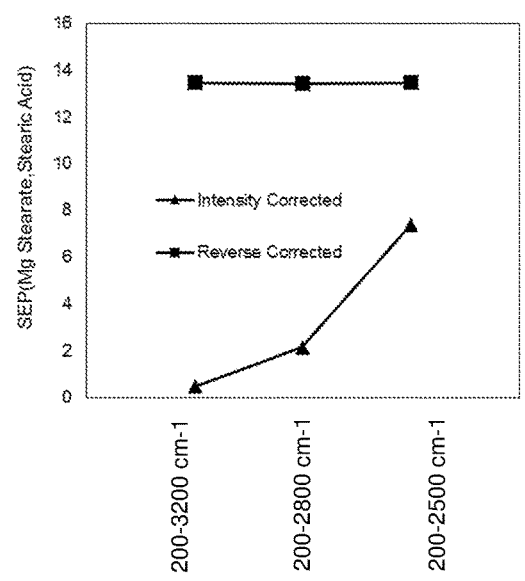
FIG. 4a
FIG. 4b

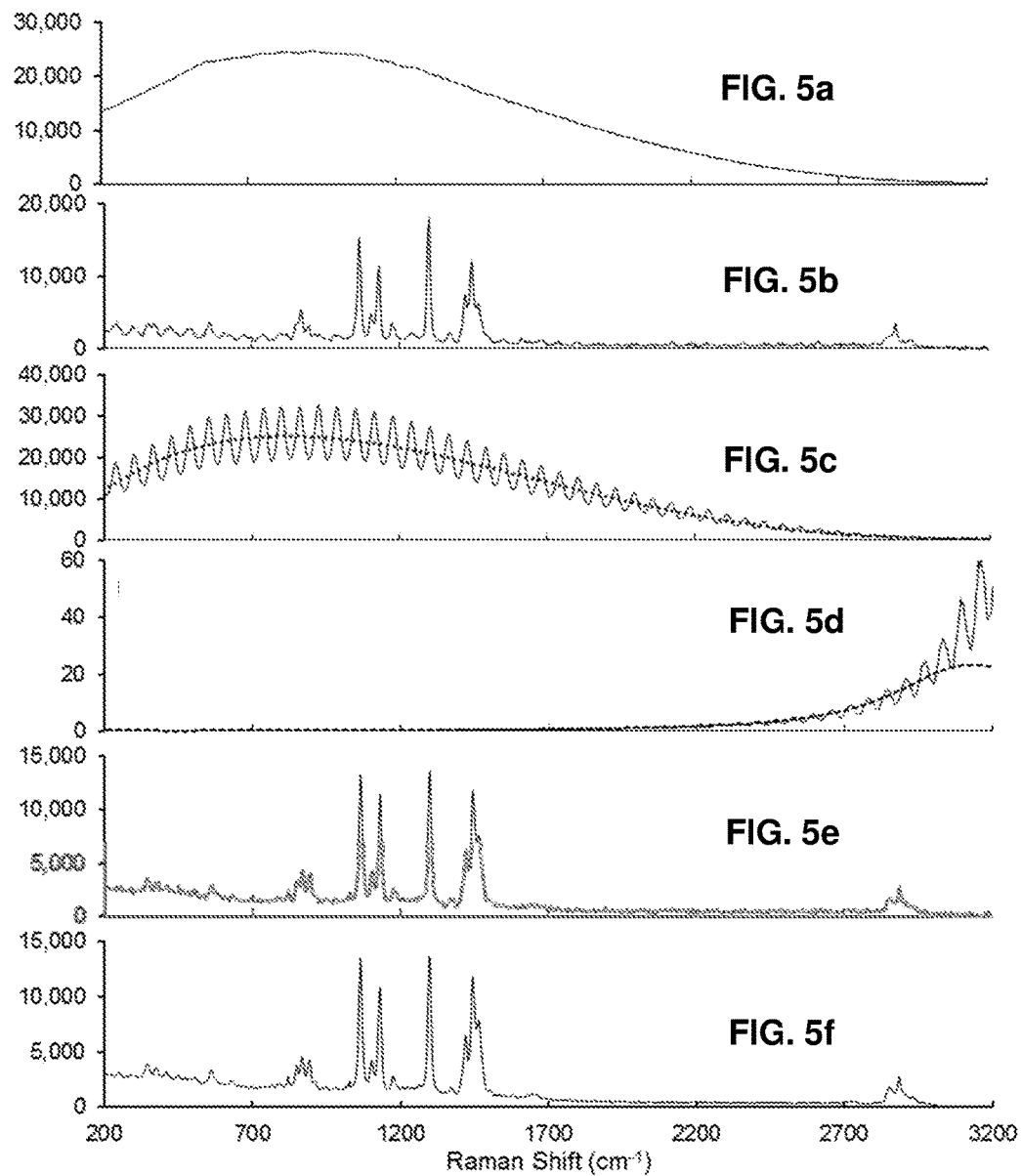

REVERSE INTENSITY CORRECTION FOR RAMAN SPECTRAL LIBRARY SEARCH

REFERENCE TO RELATED APPLICATION

This application claims inventions which were disclosed in Provisional Patent Application No. 62/418,828, filed Nov. 8, 2016, entitled "REVERSE INTENSITY CORRECTION FOR RAMAN SPECTRAL LIBRARY SEARCH". The benefit under 35 USC § 119(e) of the above mentioned United States Provisional Application is hereby claimed, and the aforementioned application is hereby incorporated herein by reference.

FIELD OF THE INVENTION

This invention generally relates to Raman spectroscopy, and more specifically to a reverse intensity correction method for Raman spectral library search.

BACKGROUND

Raman spectroscopy is gaining widespread acceptance as a chemically specific identification tool, as manifested by the rapid growth of handheld analyzers in the past decade. A commonly used method to identify unknown material is searching through spectral libraries by means of hit quality index (HQI). Frequently the test spectra and the library spectra are acquired on different instruments. For meaningful comparison, such spectra must be intensity corrected to calibrate out the unit to unit variations in spectral response. Earlier methods developed to standardize relative Raman spectral intensities used white light irradiance sources. McCreery's group pioneered the work of using luminescent glass as a convenient source that can easily reproduce the sampling condition. This methodology was later adopted by the National Institute of Standards and Technology, which now produces certified luminescent glass relative intensity standards for various excitation wavelengths. Both white light and luminescence standards are used presently in research and commercial instrumentation, and have facilitated meaningful comparison of Raman spectra acquired on different instruments, even of different excitation wavelengths. Consequently, commercial Raman spectral libraries are all standardized with relative intensity correction.

To match with the standardized library spectra, the sample spectrum acquired on a test instrument must also be corrected for the instrument response. This is a widely accepted practice, and is incorporated in most commercial Raman library search algorithms. However, there is a side effect with this approach, that is, the intensity correction magnifies the contribution to the HQI from spectral regions of lower responsivity, where the signal to noise ratio (SNR) is often poor. As will be demonstrated in this manuscript, this results in reduced specificity. This effect is particularly prominent in handheld analyzers using NIR excitations and CCD detectors, where the instrument response often varies greatly across the spectral range, and SNRs in the low responsivity regions are typically poor.

SUMMARY OF THE INVENTION

It is the goal of the present invention to provide an alternative approach of spectral intensity correction toward HQI computation. Instead of applying the NIST recommended intensity correction to the test spectra to match the standardized library spectra, the instrument's response curve is applied in reverse to the standardized library spectra to match the uncorrected test spectra. This Reverse Intensity Correction (RIC) method and its variant Modified Reverse Intensity Correction (MRIC) significantly improves spectral search performance for instruments with relatively high hardware noise and highly varying response curves, which is typical of handheld CCD Raman analyzers with NIR excitations.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 1a to FIG. 1f show the reduced precision in HQI caused by magnified noise as a result of the relative intensity correction of the sample spectrum of benzonitrile, in which FIG. 1a shows the uncorrected spectrum; FIG. 1b shows the instrument response curve; FIG. 1c shows the intensity corrected spectrum; FIG. 1d shows the intensity corrected benzonitrile library spectrum; FIG. 1e shows the HQI values of 20 consecutive scans using the spectral range from 200 to 3200 cm-1; and FIG. 1f shows the HQI values of the same 20 scans using the spectral range from 200 to 2800 cm-1;

FIG. 2a to FIG. 2h show a spectral comparison of the standard intensity correction and the reverse intensity correction of two weak Raman scatterers, magnesium stearate and stearic acid measured through 0.057 mm thick polyethylene bags, in which FIG. 2a and FIG. 2e are the uncorrected sample spectra; FIG. 2b and FIG. 2f are the intensity corrected sample spectra; FIG. 2c and FIG. 2g are the library spectra; and FIG. 2d and FIG. 2h are reverse intensity corrected library spectra for magnesium stearate and stearic acid, respectively;

FIG. 3a to FIG. 3f show the HQI values of 20 magnesium stearate spectra and 20 stearic acid spectra using the standard intensity correction of sample spectra in comparison with using the Reverse Intensity Correction of library spectra at 3 different spectral ranges, in which FIG. 3a and FIG. 3d show the HQI values for the spectral range from 200 to 3200 $cm^{-1}$; FIG. 3b and FIG. 3e show the HQI values for the spectral range from 200 to 2800 $cm^{-1}$; and FIG. 3c and FIG. 3f show the HQI values for the spectral range from 200 to 2500 $cm^{-1}$ using the standard intensity correction method and the Reverse Intensity Correction method, respectively (note the difference in scale);

FIG. 4a and FIG. 4b show the separating power (SEP) using the standard intensity correction and Reverse Intensity Correction at 3 different spectral ranges, in which FIG. 4a shows the SEP of stearic acid from magnesium stearate and FIG. 4b shows the SEP of magnesium stearate from stearic acid;

FIG. 5a to FIG. 5e demonstrate periodic modulation in response curve and MRIC, with modulation depth of 0.25, in which FIG. 5a is the measured NIST SRM 2241 luminescence spectrum; FIG. 5b is the simulated uncorrected spectrum of stearic acid; FIG. 5c is the simulated NIST SRM 2241 spectrum (solid curve) and the $4^{th}$ order polynomial fit (dotted smooth curve); FIG. 5d is the response curve C (solid curve) and modified response curve C' (dotted smooth curve); FIG. 5e is the $S'_{UC}$ calculated per equation (5); and FIG. 5f is the $L'_{RC}$ calculated per equation (6)

Figure 3A:
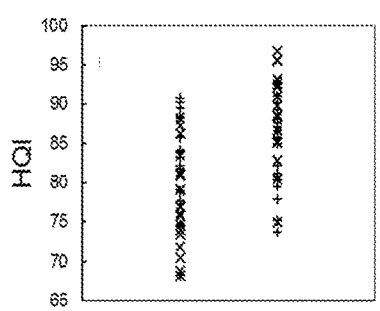
Figure 3B:
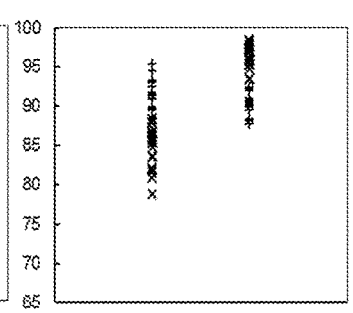
Figure 3C:
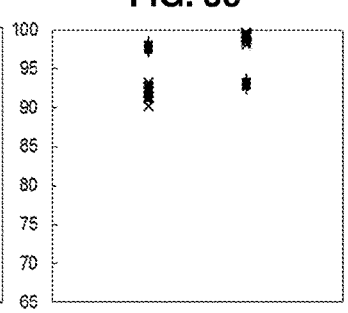

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a reverse intensity correction method for Raman spectral library search. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Theory

The instrument response curve C of a Raman spectrometer is obtained by measuring a spectrum M of a standard source of known spectral shape I:

$$C = \frac{1}{M} \quad (1)$$

Here the division is operated point-to-point. An intensity corrected Raman spectrum $S_C$ of a sample is obtained by measuring its uncorrected Raman spectrum $S_{UC}$, and multiplying the response curve C.

$$S_C = S_{UC} \cdot C \quad (2)$$

This is compared with intensity corrected library spectrum $L_C$ to yield a hit quality index for library searching. In practice, the derivative of the spectra are normally used, to remove the influence of backgrounds.

Reverse Intensity Correction algorithm works in a similar way, except that the standardized library spectrum is corrected with the inverse of the response curve of the test instrument (not necessarily the instrument that measured the library spectrum), $$L_{RC} = \frac{L_C}{C} \quad (3)$$

and the hit quality index for the pair $(S_{UC}, L_{RC})$ is used to rank the library candidates.

Typically the spectra in commercial libraries are collected on high performance instruments with sufficient intensity to provide good SNR over the entire spectral range, such that applying RIC to $L_C$ does not produce significant side effect due to noise magnification. The spectrum $L_{RC}$ represents what would be obtained if the library spectrum was acquired on the test instrument without intensity correction, which is now directly comparable with test spectrum $S_{UC}$. Some instruments incorporates filters or back thinned CCD sensors that have etaloning effects which cause periodic modulations to the response curve. The standard intensity correction process when done properly has the benefit of removing such modulations, which would be difficult to deal with by other means. The RIC method in this case would suffer from unremoved modulation that may negatively impact the results. We realize that whatever correction curve is applied to the test or library spectra, the end effect is assigning weighting factors to the spectral elements toward HQI calculation. The standard intensity correction applies higher weights to the lower responsivity (and frequently low SNR) region of the test spectrum, while the RIC method keeps the test spectrum unchanged, i.e. applies a flat curve to avoid magnifying the noisy region. Therefore the straight RIC procedure can be modified such that it first performs the standard intensity correction which will remove the modulation, followed by the division of a weighting curve that is free of such modulations yet models the overall response curve shape. If we fit the measured spectrum M with a low order polynomial, or smooth it sufficiently, we can obtain a modulation free spectrum M'. A modified smooth response curve C' that reflects the overall shape of the response curve C can be obtained by $$C' = \frac{1}{M'} \quad (4)$$

The MRIC works by forward correcting the test spectrum $S_{UC}$ with C, and then reverse correcting the result, along with the library spectrum $L_C$, with C':

$$S'_{UC} = \frac{S_{UC} \cdot C}{C'} \quad (5)$$

$$L'_{RC} = \frac{L_C}{C'} \quad (6)$$

The HQI between the pair $(S'_{UC}, L'_{RC})$ is then used for quantify their similarity. It will be demonstrated through simulation that the MRIC procedure achieves the dual purpose of removing the modulation and maintaining the overall shape of the instrument response curve.

The performance of an HQI algorithm can be measured by how well it can separate spectrally similar compounds. If a large number of tests are performed using compound A and B, and the HQI is calculated against their library spectra, then we can define a parameter Separating Power of A from B as:

$$SEP(A, B) = \frac{\overline{HQI(A \mid A)} - \overline{HQI(A \mid B)}}{\delta_{A \mid A} + \delta_{A \mid B}} \quad (7)$$

Where $\overline{HQI(A|B)}$ and $\delta_{A|B}$ are the mean and standard deviation of the HQI values of test compound A against library candidate B. Normally, $\overline{HQI(A|B)} \leq \overline{HQI(A|A)}$, and Separating Power is nonnegative. In general, A and B are not commutable. The higher the SEP, the better the separation. Given the same test data set, the algorithm that yields higher SEP will in general produce a higher specificity.

Experiment

All chemicals used are reagent grade and purchased from Sigma Aldrich. NIST SRM 2241 luminescence standard was purchased from NIST.

Solid materials were placed inside 0.057 mm thick low density polyethylene bags and their Raman spectra acquired through the bag. Liquid samples were placed inside glass vials and measured using the glass vial adaptor. Being able to identify contents without opening the container is a key advantage of Raman over some other analytical techniques, and this is how handheld Raman analyzers are typically used by end users.

The instrument performance, including the Raman shift and the overall Raman intensity was validated prior to use with the supplied polystyrene sample and the built-in validation function.

Benzonitrile spectra were measured using a handheld analyzer TacticID (B&W Tek) and a liquid vial adaptor. The analyzer is equipped with a CCD sensor and a CW 785 nm laser with an unpolarized output of 300 mW at full power. The CCD temperature was not controlled and was well above the ambient during operation. All other spectra were measured using a handheld analyzer NanoRam (B&W Tek), which is equipped with a temperature controlled CCD sensor and a laser of the same specification as the TacticID. Both analyzers have the same specified spectral range of 176-2900 $cm^{-1}$, but the actual spectral coverages extend beyond 3200 $cm^{-1}$. The spectrograph resolution measured as the FWHM of the 912 nm argon emission line was 7.3 $cm^{-1}$ and 8.6 $cm^{-1}$ for the TacticID and NanoRam, respectively, and the Raman resolution measured using the 1085 $cm^{-1}$ calcite peak according to ASTM E2529-06 was 9.6 $cm^{-1}$ and 9.1 $cm^{-1}$, respectively. The laser power was set to 90% for all measurements, and the integration time was automatically controlled to produce at least 20,000 counts at the pixel of strongest intensity. For benzonitrile, this was typically 0.5 to 1.0 seconds. For the stearic acid and magnesium stearate samples, this was typically 10 to 20 seconds. After each Raman acquisition, the laser was immediately turned off and a dark spectrum automatically acquired with the same integration time. The dark spectrum was subtracted from the Raman spectrum to yield the pure Raman spectrum.

The intensity correction curve for each instrument was obtained by measuring the spectrum of the luminescence standard, and applying the intensity polynomial supplied by NIST. For HQI calculation, spectra are first interpolated to 4 $cm^{-1}$ spacing, and then their $2^{nd}$ derivatives are calculated using the Savitzky-Golay filters. The Pearson Correlation Coefficient of the two derivative spectra was used as the HQI. As is known to those skilled in the art, there are a multitude of search algorithms that compare the test spectrum with the library spectra for best match, for example, methods based on spectral correlation, Euclidean distance, least square (see S. R. Lowry, "automated Spectral Searching in Infrared, Raman and Near-Infrared spectroscopy", J. Wiley & Sons, pp 1948-1961), sum of absolute difference, and vector dot product (see J. B. Loudermilk et al, "Novel Search Algorithms for a Mid-Infrared Spectral Library of Cotton Contaminants", Applied Spectroscopy, Volume 62, Number 6, 2008).

Results in FIGS. 1 through 4 are obtained by downloading the spectra from the analyzers and processing in Excel using VB programs. The library spectra in these figures were obtained by averaging 20 scans and the test spectra were all single scans. Results in Table 1 were obtained using the Investigation mode of the NanoRam's onboard software NOS. The standard intensity correction algorithm was implemented in NOS V5.12. A library containing the test compounds was created in NOS V5.12 using the onboard Library utility, where each library spectrum was the average of 3 scans. Twenty scans of each test compounds were performed using the Investigation mode and the HQI values recorded. The NOS was then upgraded to V5.14, which implemented the RIC algorithm, and another 20 scans taken.

Simulation

Etaloning effect is simulated by multiplying a sine wave $y=1+depth \cdot sin(\omega x)$ (where $\omega$ is the angular modulation frequency which is set to $0.1/cm^{-1}$, and x is the Raman shift in $cm^{-1}$) to the measured Raman spectra and the luminescence spectrum of a NIST 2241 standard material. Modulation free spectrum M' of the NIST 2241 standard is obtained by fitting its modulated spectrum M with a $4^{th}$ order polynomial. The response curve C and the modified response curve C' are then obtained via equations (1) and (4), respectively. The parameter "depth" is varied and HQIs are calculated using both the RIC and MRIC algorithms.

Results and Discussion

FIG. 1a to FIG. 1f illustrate the noise magnification effect of the standard intensity correction procedure. FIG. 1a and FIG. 1c are representative spectra of benzonitrile before and after intensity correction, respectively. Comparing with the library spectrum shown in FIG. 1d, it is obvious the response toward the higher Raman shift end is significantly lower than the finger print region, as manifested by the response curve shown in FIG. 1b. The intensity correction magnifies the 3072 $cm^{-1}$ peak and makes the overall spectral shape similar to the library, and results in a correlation coefficient improvement from 0.59 between FIG. 1a and FIG. 1d to 0.96 between FIG. 1c and FIG. 1d. However, noise in this region is equally magnified. This results in a large scattering in the HQI of the 20 scans, as shown in FIG. 1e. If the most noisy region between 2500 and 3200 $cm^{-1}$ is excluded from the calculation, then the precision is greatly improved, as shown in FIG. 1f. The standard deviation of the HQI in FIG. 1e and FIG. 1f are 0.012 and 0.0004, respectively. The average HQI also sees a moderate improvement, from 0.972 to 0.989.

Figure 3D:
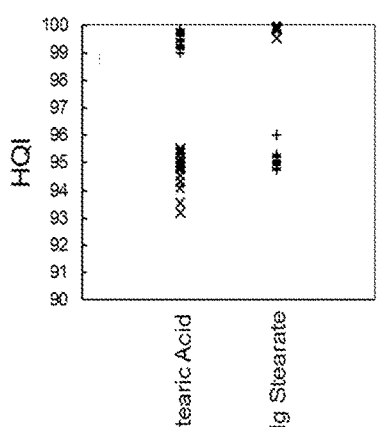

As library search relies on clear separation in HQI to distinguish search candidates, it can be expected that the poor precision induced by the magnified noise will cause degradation in the specificity of the search, and this would be particularly problematic for weak Raman scattering samples. FIG. 2a to FIG. 2h illustrate this effect. The spectra shown in FIG. 2a and FIG. 2e are spectra of magnesium stearate and stearic acid powders contained in 0.057 mm thick low density polyethylene bags. Although polyethylene itself has a spectrum that is very similar to the two compounds of interest, its intensity contribution to the measured spectra is estimated to be less than 5%. Visual inspection of the uncorrected spectra in FIG. 2a and FIG. 2e indicates the two compounds have similar but distinguishable Raman features. However, their difference is diminished after the intensity correction, as shown in both test spectra in FIG. 2b and FIG. 2f as well as library spectra in FIG. 2c and FIG. 2g. This is mainly due to their very similar features in the CH stretch region, which is magnified significantly along with the noise. Indeed, the HQI values of the total of 40 intensity corrected scans against the library spectra in FIG. 2c and FIG. 2g are thoroughly mixed, as shown in FIG. 3a. In contrast, the HQI values of the same 40 scans are clearly separated into two groups for each of the two reverse corrected library spectra in FIG. 2d and FIG. 2h, as shown in FIG. 3d.

Figure 3E:
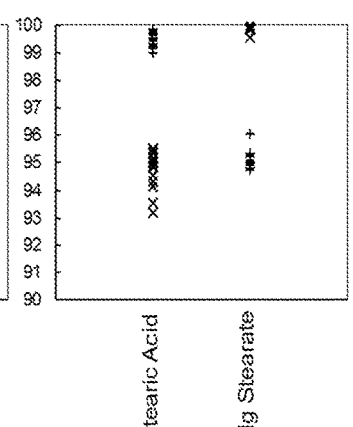
Figure 3F:
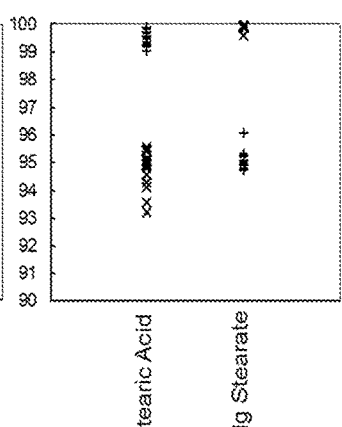

If the poor results in FIG. 3a are due to the magnified noise, then the separating power of the standard algorithm should improve as the high end of the spectral range is successively reduced, although this would come with the risk of losing useful information for unknown samples and is therefore undesirable. Nevertheless, this is verified in FIG. 3b and FIG. 3c. In contrast, the separating power of the RIC algorithm is largely invariant, as shown in FIG. 3d, FIG. 3e, and FIG. 3f, and further quantified in FIG. 4a and FIG. 4b.

Figure 6:
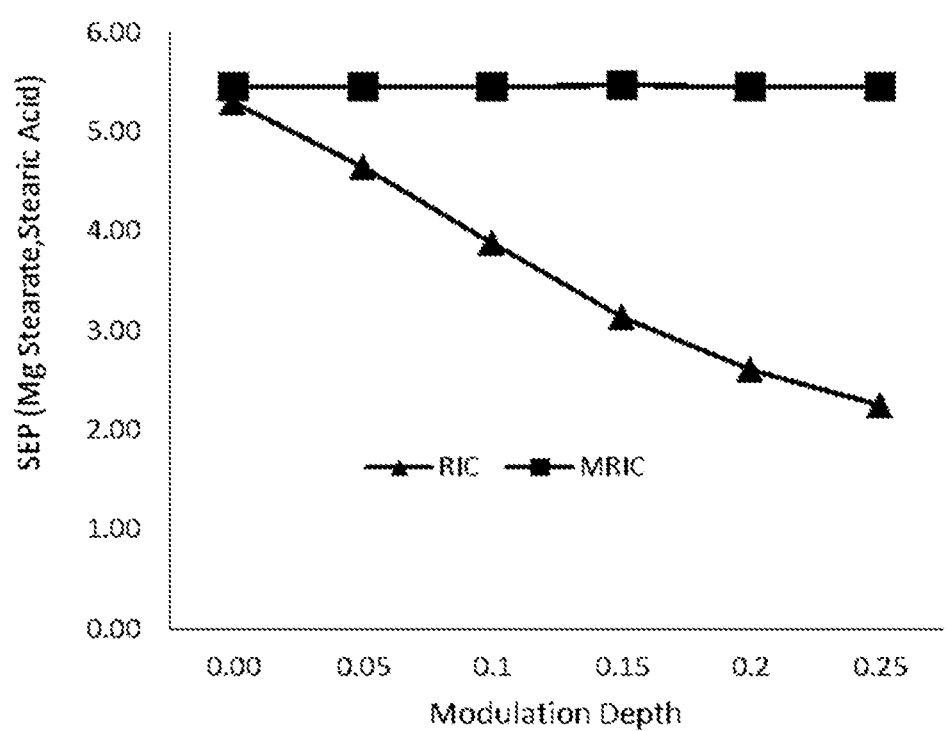
FIG. 6 shows the Separating Power as a function of response curve modulation depth for both RIC and MRIC algorithms.

The effect of periodic modulation in the response curve is simulated and presented in FIG. 5a to FIG. 5e. FIG. 5a is the measured NIST SRM 2241 spectrum. A sine curve is multiplied with the spectrum in FIG. 5a to obtain a simulated NIST SRM 2241 spectrum M shown in FIG. 5c with a modulation depth 0.25. A $4^{th}$ order polynomial fitting of M provides the modified NIST SRM 2241 spectrum M'. The same sine curve is multiplied with a measured spectrum of stearic acid to obtain the simulated sample spectrum $S_{UC}$ as shown in FIG. 5b. The response curve C and the modified response curve C' are calculated according to equations (1) and (4), and shown in FIG. 5d. The modified sample spectrum $S'_{UC}$ is calculated using equation (5), and shown in FIG. 5e. The reverse corrected library spectrum $L'_{RC}$ shown in FIG. 5f is calculated using equation (6), where the library spectrum in FIG. 2g is used as $L_C$. HQI with the straight RIC method is calculated using $S_{UC}$ and $L_{RC}$ (not shown). HQI with the MRIC method is calculated using $S'_{UC}$ and $L'_{RC}$. The resulting separating power SEP (stearic acid, magnesium stearate) is displayed in FIG. 6. Clearly, as the modulation depth increase, the performance of the RIC method degrades, while the MRIC remains constant, and always better than RIC. Even without the added modulation, the MRIC method yields SEP=5.45, which is slightly better than the RIC's 5.30. This is because the as measured NIST SRM 2241 spectrum 5(a) already contains a slight modulation. Although not shown, SEP (magnesium stearate, stearic acid) has a similar trend.

Table 1 compares the HQI values of several compounds measured with the standard intensity correction algorithm and with RIC using a spectral range from 176 to 2500 cm$^{-1}$. These include very strong scatterers with low fluorescence such as cyclohexane and very weak scatters with high fluorescence such as cellulose. As shown, the precision is improved for all samples using the RIC method, as demonstrated by the varying amount of reduction in the standard deviation. The average HQI also increases slightly, with cellulose being a notable exception. The large increase in HQI average for cellulose is due to its high fluorescence background, which results in low SNR. Using the ratio of mean HQI over its standard deviation as a measure of resolving power, this is improved by 37% for sucrose to 2223% for cyclohexane.

TABLE 1

Performance comparison of standard intensity correction and reverse intensity correction for Raman spectral library search

| | Intensity Corrected | | | Reverse Intensity Corrected | | | % |
|---|---|---|---|---|---|---|---|
| | Mean | STD | Mean/STD | Mean | STD | Mean/STD | Improvement |
| hypromellose | 0.971 | 0.00746 | 130.2 | 0.986 | 0.00371 | 265.8 | 104 |
| cellulose | 0.63 | 0.05817 | 10.8 | 0.852 | 0.0212 | 40.2 | 271 |
| caffeine | 0.996 | 0.00135 | 737.8 | 0.999 | 0.00018 | 5550.0 | 652 |
| sucrose | 0.971 | 0.02034 | 47.7 | 0.977 | 0.01491 | 65.5 | 37 |
| sodium bicarbonate | 0.998 | 0.00074 | 1348.6 | 1 | 0.0001 | 10000.0 | 641 |
| cyclohexane | 0.994 | 0.00208 | 477.9 | 0.999 | 0.00009 | 11100.0 | 2223 |
| ethanol | 0.998 | 0.00063 | 1584.1 | 1 | 0.00008 | 12500.0 | 689 |

CONCLUSION

The standard intensity correction method gives more weight to spectral regions where the instrument responsivity is lower, which results in reduced separating power that varies with spectral coverage, and therefore poor search performance. The performance can be improved by sacrificing the spectral region of lower responsivity. The RIC method including its modified version MRIC achieves improved HQI precision and separating power over the standard intensity correction method without sacrificing the spectral range. It does so by giving roughly equal weights to all spectral elements. The RIC method requires no extra information, and can be easily implemented, and is useful for library searching using commercial spectral libraries.

It is to be understood that the instrument response curve can be represented differently, using the inverse of C instead. An intensity corrected Raman spectrum $S_C$ of a sample is then obtained by measuring its uncorrected Raman spectrum $S_{UC}$, and dividing the response curve. Such mathematically equivalent forms of representations are considered identical to each other.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A Raman spectral analysis method for identifying a sample, said sample being measured by a Raman spectrometer to obtain an uncorrected Raman spectrum, the method comprising the steps of:
   receiving the uncorrected Raman spectrum of the sample;
   obtaining an instrument response curve;
   reversely correcting standard spectra in a standard Raman spectral library using the instrument response curve to produce a reversely corrected Raman spectral library, wherein the reversely corrected Raman spectral library includes at least one reversely corrected Raman spectrum; and
   identifying the sample using the uncorrected Raman spectrum of the sample and the at least one reversely corrected Raman spectrum.

2. The Raman spectral analysis method of claim 1, wherein identifying the sample using the uncorrected Raman spectrum of the sample and the at least one reversely corrected Raman spectrum comprises determining a correlation coefficient between the two spectra.

3. The Raman spectral analysis method of claim 1, wherein the instrument response curve used to reversely correct the Raman spectral library is the instrument response curve of the Raman spectrometer.

4. The Raman spectral analysis method of claim 1, wherein the instrument response curve used to reversely correct the Raman spectral library is a modified instrument response curve, and wherein the modified instrument response curve is derived from an instrument response curve of the Raman spectrometer by using a polynomial or by smoothing the instrument response curve.

5. The Raman spectral analysis method of claim 1, wherein the uncorrected Raman spectrum of the sample is modified by the ratio of the modified instrument response curve to the instrument response curve before determining the correlation coefficient between the modified Raman spectrum of the sample and the at least one reversely corrected Raman spectrum.

6. A method for identifying a sample using Raman spectral analysis, said sample being measured by a Raman spectrometer to obtain an uncorrected Raman spectrum, the method comprising the steps of:
   receiving the uncorrected Raman spectrum of the sample;
   obtaining an instrument response curve of the Raman spectrometer and deriving a modified instrument response curve from the said instrument response curve;
   modifying the uncorrected Raman spectrum of the sample using the ratio of the modified instrument response curve to the instrument response curve;
   reversely correcting a standard Raman spectral library using the modified instrument response curve to obtain a reversely corrected Raman spectral library, wherein the reversely corrected Raman spectral library includes at least one reversely corrected Raman spectrum; and
   identifying the sample by comparing the modified uncorrected Raman spectrum of the sample and the at least one reversely corrected Raman spectrum in the library.

7. The method of claim 6, wherein the modified instrument response curve is obtained by fitting the instrument response curve with a polynomial or by smoothing the instrument response curve.

8. The method of claim 6, wherein the step of identifying the sample comprises determining a correlation coefficient between the modified uncorrected Raman spectrum of the sample and the at least one reversely corrected Raman spectrum in the reversely corrected Raman spectral library.

9. An apparatus for identifying a sample using Raman spectral analysis, said sample being measured by a Raman spectrometer to obtain an uncorrected Raman spectrum, the apparatus comprising:
   an input device for receiving the uncorrected Raman spectrum of the sample;
   memories for storing an instrument response curve of the Raman spectrometer and a standardized Raman spectral library; and
   one or more processors configured to:
      reversely correct standard spectra in the standard Raman spectral library to compensate for deviations caused by the Raman spectrometer to obtain a reversely corrected Raman spectral library, wherein the reversely corrected Raman spectral library includes at least one reversely corrected Raman spectrum; and
      identify the sample using the uncorrected Raman spectrum of the sample and the at least one reversely corrected Raman spectrum.

10. The apparatus of claim 9, wherein the one or more processors are configured to determine a correlation coefficient between the uncorrected Raman spectrum of the sample and the at least one reversely corrected Raman spectrum to identify the sample.

11. The apparatus of claim 9, wherein the one or more processors are configured to derive the at least one reversely corrected Raman spectrum by reversely applying the instrument response curve to the standard Raman spectral library.

12. The apparatus of claim 9, wherein the one or more processors are configured to derive the at least one reversely corrected Raman spectrum from the standard Raman spectra library using a modified instrument response curve.

13. The apparatus of claim 12, wherein the one or more processors are configured to modify the uncorrected Raman spectrum of the sample by the ratio of the modified instrument response curve to the instrument response curve before determining the correlation coefficient between the uncorrected Raman spectrum of the sample and the at least one reversely corrected Raman spectrum.

14. A non-transitory computer-readable medium storing a program, when the program is executed by a computing device, causing the computing device to:
   receive an uncorrected Raman spectrum of the sample measured by a Raman spectrometer;
   obtain an instrument response curve;
   reversely correct standard spectra in the standard Raman spectral library to compensate for deviations caused by the Raman spectrometer using the instrument response curve to obtain a reversely corrected Raman spectral library, wherein the reversely corrected Raman spectral library includes at least one reversely corrected Raman spectrum; and
   identify the sample using the uncorrected Raman spectrum of the sample and the at least one reversely corrected Raman spectrum.

15. The non-transitory computer-readable medium of claim 14, wherein the program, when executed by the computing device, further causes the computing device to determine a correlation coefficient between the uncorrected Raman spectrum of the sample and the at least one reversely corrected Raman spectrum to identify the sample.

16. The non-transitory computer-readable medium of claim 15, wherein the instrument response curve used to reversely correct the Raman spectral library is the instrument response curve of the Raman spectrometer.

17. The non-transitory computer-readable medium of claim 15, wherein the instrument response curve used to reversely correct the Raman spectral library is a modified instrument response curve, and wherein the modified instrument response curve is derived from an instrument response curve of the Raman spectrometer by using a polynomial or by smoothing the instrument response curve.

18. The non-transitory computer-readable medium of claim 15, wherein the uncorrected Raman spectrum of the sample is modified by the ratio of the modified instrument response curve to the instrument response curve, before determining the correlation coefficient between the modified Raman spectrum of the sample and the at least one reversely corrected Raman spectrum.

* * * * *